(12) United States Patent
Dunkley et al.

(10) Patent No.: US 9,975,770 B2
(45) Date of Patent: *May 22, 2018

(54) OZONE GENERATOR DEVICE

(71) Applicant: DOW GLOBAL TECHNOLOGIES LLC, Midland, MI (US)

(72) Inventors: Peter Dunkley, Birlingham (GB); Kenneth John Soper, Worcester (GB)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/727,147

(22) Filed: Jun. 1, 2015

(65) Prior Publication Data

US 2015/0259204 A1    Sep. 17, 2015

Related U.S. Application Data

(62) Division of application No. 13/394,581, filed as application No. PCT/GB2010/001693 on Sep. 7, 2010, now Pat. No. 9,078,941.

(30) Foreign Application Priority Data

Sep. 7, 2009    (GB) .................................. 0915484.0

(51) Int. Cl.
*C01B 13/11*    (2006.01)
*A61L 2/20*    (2006.01)
(Continued)

(52) U.S. Cl.
CPC ............ *C01B 13/115* (2013.01); *A61L 2/202* (2013.01); *A61L 9/015* (2013.01); *A61L 9/12* (2013.01);
(Continued)

(58) Field of Classification Search
CPC ............ A61L 2/202; A61L 9/015; A61L 9/12; A61L 2202/11; A61L 2202/25;
(Continued)

(56) References Cited

U.S. PATENT DOCUMENTS 3,798,457 A    3/1974   Lowther
3,925,673 A *  12/1975  Wright, Jr. ............. B01J 19/088
                                                250/432 R
(Continued)

FOREIGN PATENT DOCUMENTS

EP    1500404       1/2005
JP    04-021503     1/1992
(Continued)

OTHER PUBLICATIONS

Japanese Office Action, Application No. 2012-528442, dated Sep. 9, 2014 (English translation).

(Continued)

*Primary Examiner* — Xiuyu Tai

(57) ABSTRACT

An ozone generator cartridge 60 suitable for a sterilization, decontamination and/or sanitation device. The cartridge comprises a sealable housing 60 for providing a corona discharge, the housing containing at least one power supply unit 64 and at least one inlet 65 for connection to an oxygen or air supply, the cartridge including at least part of at least one ozone conversion cell 63 attached to and extending from an external surface of a wall of the sealed housing, the conversion cell extending into a delivery conduit 52 of a decontamination device that leads to at least one discharge outlet 16.

6 Claims, 6 Drawing Sheets

(51) Int. Cl.
*A61L 9/015* (2006.01)
*A61L 9/12* (2006.01)

(52) U.S. Cl.
CPC ............ *C01B 13/11* (2013.01); *A61L 2202/11* (2013.01); *A61L 2202/25* (2013.01); *C01B 2201/22* (2013.01); *C01B 2201/32* (2013.01); *C01B 2201/62* (2013.01); *C01B 2201/64* (2013.01)

(58) Field of Classification Search
CPC ... A61L 9/16; A61L 9/22; C01B 13/11; C01B 13/115; C01B 2201/32; C01B 2201/64; C01B 2201/22; C01B 2201/62; C01B 13/00; C01B 2201/12; C01B 2201/10; B01D 2259/818; B01D 53/32; B01J 19/088; H01T 23/00
See application file for complete search history.

(56) References Cited

U.S. PATENT DOCUMENTS

| | | |
|---|---|---|
| 2002/0098109 A1 | 7/2002 | Nelson et al. |
| 2003/0175180 A1* | 9/2003 | Shannon ................ A61L 9/015 422/186 |
| 2006/0018810 A1 | 1/2006 | Taylor et al. |
| 2006/0018811 A1 | 1/2006 | Taylor et al. |
| 2008/0031770 A1 | 2/2008 | Heselton et al. |
| 2008/0047907 A1 | 2/2008 | Herzog |
| 2009/0120863 A1* | 5/2009 | Salama ................ C02F 1/46109 210/192 |

FOREIGN PATENT DOCUMENTS

| | | |
|---|---|---|
| JP | 2000-001304 | 7/2000 |
| JP | 2001-286542 | 10/2001 |
| JP | 2004-166743 | 6/2004 |
| WO | 2000/074197 | 12/2000 |

OTHER PUBLICATIONS

Search Report issued by the UK Intellectual Property Office dated Jan. 6, 2010 in UK Patent Application No. GB0915484.0.

Foreign Communication From a Related Counterpart Application—India Office Action, India Application No. 3032/CHENP/2012, dated Mar. 4, 2012, 6 pages.

* cited by examiner

OZONE GENERATOR DEVICE

This invention relates to an ozone generator cartridge, particularly but not exclusively for an improved sterilisation, sanitisation and/or decontamination device.

It is a requirement to sterilise and sanitise enclosed spaces, such as kitchen areas and hospital rooms quickly and effectively, to destroy potentially harmful micro-organisms, such as bacteria and viruses, contaminating the air and surfaces there within, in an acceptable timescale.

The biocidal activity of ozone is widely known and appreciated, and it is also known that the provision of ozone in a humid atmosphere increases the biocidal effectiveness.

However, problems associated with the use of ozone as a biocide have been the relatively lengthy post-treatment process to ensure that the environment is safe for returning occupants, the use of potentially environmentally damaging chemicals during the process, the general ineffectiveness of the process package in sanitising the environment, and the overall lack of simplicity in quickly setting up and using the apparatus.

The Applicant's previous application EP 1500404 (Steritrox Limited) and GB Application No.s 0904262.3, 0904264.9, 0904266.4, 0904269.8 and 0904272.2 relate to their methods for decontamination of an environment using the beneficial effect of ozone in a humid atmosphere. Whilst these processes are efficient at providing a sterile environment, the operation of such processes in practice require a large number of internal components to be provided within a packaged product. This can lead to an undesirably large and heavy end product with limited access to the internal parts. It is desirable to provide an apparatus that allows for a compact design of machine whilst enabling easy replacement of internal components, such as the ozone generator.

The present invention seeks to provide a solution to this problem.

According to a first aspect of the present invention, there is provided an ozone generator cartridge suitable for a sterilisation, decontamination and/or sanitation device, the cartridge comprising a sealable housing for providing a corona discharge, the housing containing at least one power supply unit and at least one inlet for connection to an oxygen or air supply, the cartridge including at least part of at least one ozone conversion cell attached to and extending from an external surface of a mounting plate that defines an exterior wall of the sealed housing.

The parts of the ozone conversion cell attached to and extending from the external surface of the mounting plate of the sealed housing preferably comprise those components of the cell that generate heat during the production of ozone, more preferably, one or more electrodes, dielectric, fins and/or ozone outlets. Preferably, each ozone conversion cell is in the form of a block extending from the external surface of the mounting plate of the sealed housing. Preferably, the components of the ozone generator that must be isolated from the ozone, in particular the power supply and electrics that energise the conversion cell, are provided within the housing, preferably being attached an the internal surface of the mounting plate from which the ozone conversion cell extends.

Preferably, the housing is in the general form of an elongated box having two opposing long walls and two opposing short walls sealed by end caps. Preferably, the ozone conversion cell extends substantially orthogonally from the mounting plate of the housing.

More preferably, the housing making up the ozone generator cartridge comprises a body with a cover. The body preferably comprises a mounting plate with one long side wall and two short side walls extending substantially orthogonally from the plate. The cover preferably comprises a generally L-shaped panel, the short limb of the cover making up the opposing long side wall in the assembled housing. The components of the ozone generator that must not be exposed to high levels of ozone are fixed to the inner surface of the mounting plate which is sealable within the housing by means of the cover. The at least part of an ozone conversion cell extends from the external surface of the mounting plate.

The components may be made of any suitable material that is inert to ozone. Preferably, an aluminium oxide coating is applied to the components.

One or more air movement devices, such as fans, may be provided within the housing to aid cooling of the cartridge and prevent the build up of hot spots within the housing.

The ozone generator cartridge is a stand-alone component which may be fitted to a sterilisation, decontamination and/or sanitation device. A sterilisation, decontamination and/or sanitation device may comprise at least a humidifier unit, an ozone generator, a delivery conduit and a discharge outlet, the ozone generator comprising a sealable housing for providing a corona discharge, the housing containing at least one power supply unit and at least one inlet for connection to an oxygen or air supply, the generator including at least part of at least one ozone conversion cell attached to and extending from an external surface of the mounting plate of the sealed housing into the delivery conduit leading to the at least one discharge outlet.

Preferably, the device further includes a controller for controlling the humidifier and ozone generator units.

More preferably, the ozone generator is detachable from the delivery conduit that leads to the discharge outlet, thereby enabling its easy replacement. Preferably, a fan is provided at the base of the delivery conduit remote from the discharge outlet for moving air and ozone through the conduit and out of the discharge outlet. This provides much needed cooling of the components of the ozone conversion cell and, by convection through the surface of the sealed housing, also cools the internal components that are mounted on the internal surface of the mounting plate from which the ozone conversion cell extends. Additionally, this single fan provides forced air for feeding ozone rich air into the humidifier unit and provides increased air circulation within the target area by drawing air in at the base of the device for discharge at the top of the device.

More preferably, the external surface of the mounting plate of the ozone generator cartridge supporting the ozone conversion cell comprises a wall of the delivery conduit. Preferably, the conversion cell extends transversely across the cavity of the conduit. In a preferred embodiment, the delivery conduit is in the general shape of a rectangle having only three solid sides. The fourth side is provided by the ozone generator cartridge, more particularly the mounting plate of the body of the housing.

The sides of the delivery conduit may converge towards each other as they approach the discharge outlet. Preferably, ozone generated by the ozone generator unit is discharged through the discharge outlet comprising at least two at least partially converging plates. It is preferable for the plates to be in the form of discs.

Preferably, the humidifier comprises a water reservoir and at least one discharge nozzle for releasing water droplets as a fine spray. Preferably, the at least one discharge nozzle is attached to the upper plate of the discharge outlet, remote from the lower plate. In this manner, the water droplets are supported by the airstream discharged from the discharge outlet.

Preferably, the humidifier, water reservoir, ozone generator, controller and conduit are provided within a casing or enclosure with the discharge outlet extending from the intended upper surface of the casing. It is to be appreciated that the casing or enclosure may include additional components for optimization of the operation of the device, such as a hydrocarbon discharge unit and/or a UV catalyst, appropriate sensors, a fan, an oxygen supply and/or a water reservoir. A framework may be provided for supporting the components within the enclosure.

Embodiments of the invention will now be more specifically described, by way of example only, with reference to the accompanying drawings, in which.

Figure 1:
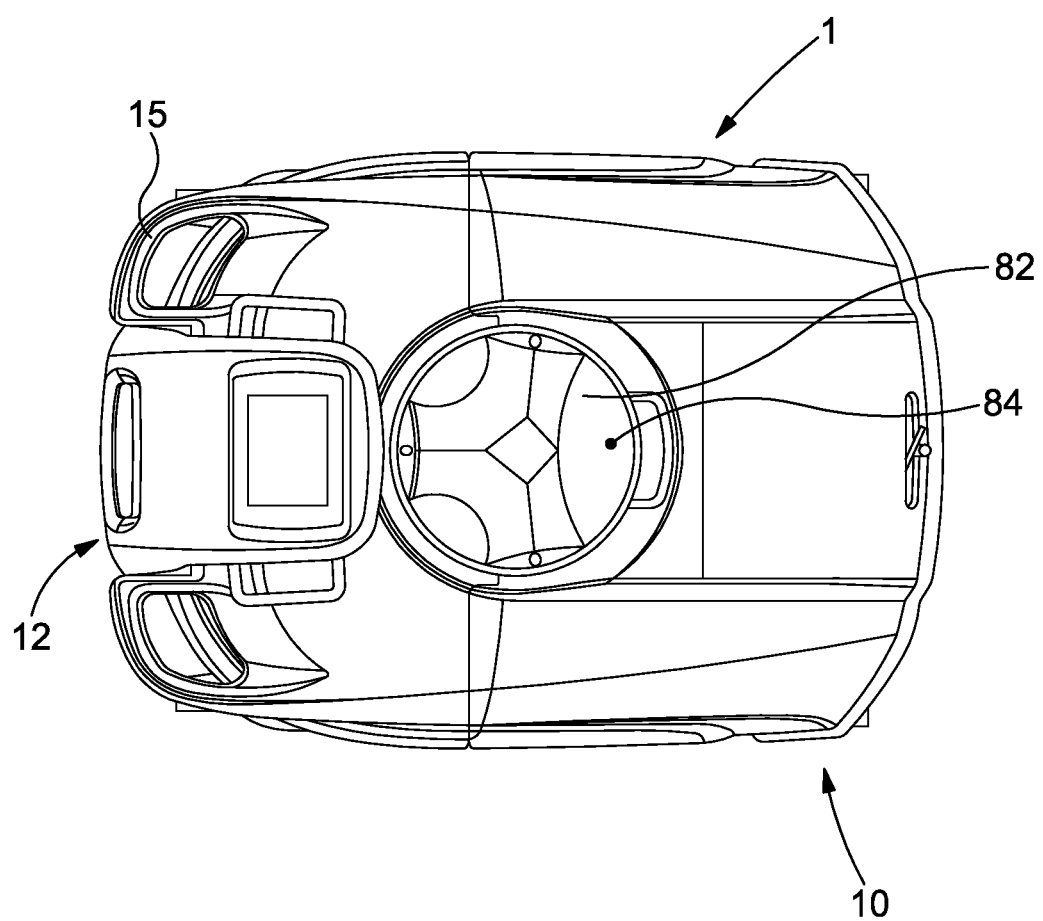
FIG. 1 is plan top elevation external view of a sterilisation and decontamination device according to an aspect related to the present invention.
Figure 2:
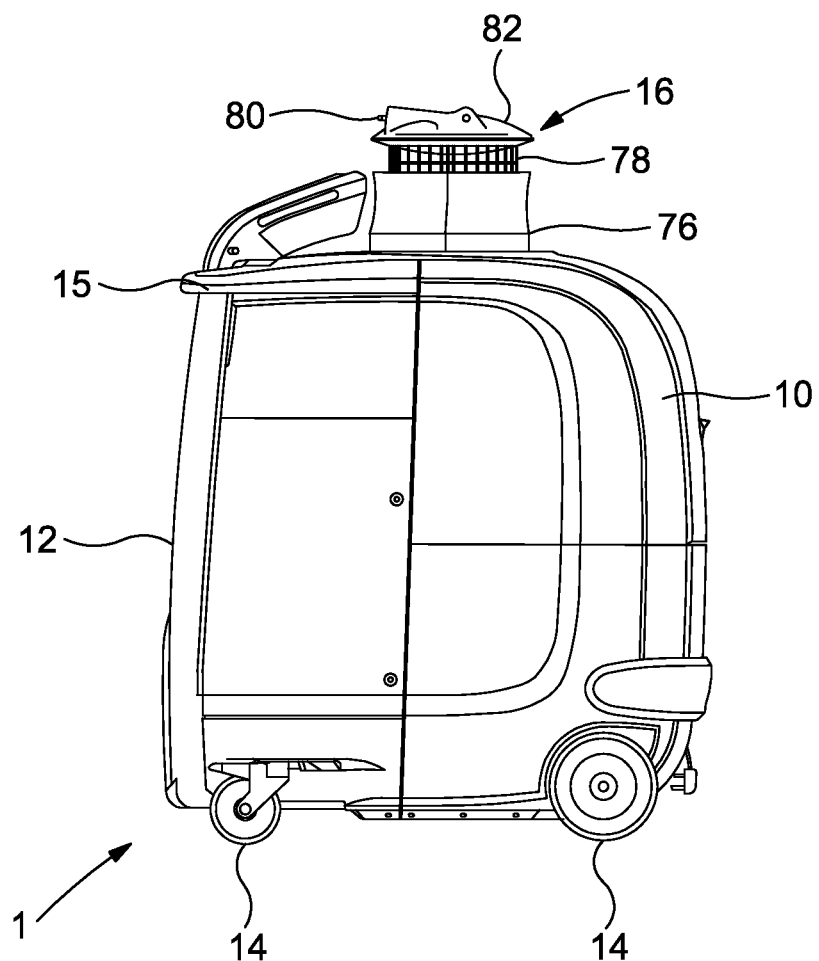
FIG. 2 is a side elevation external view of the device shown in FIG. 1.
Figure 3:
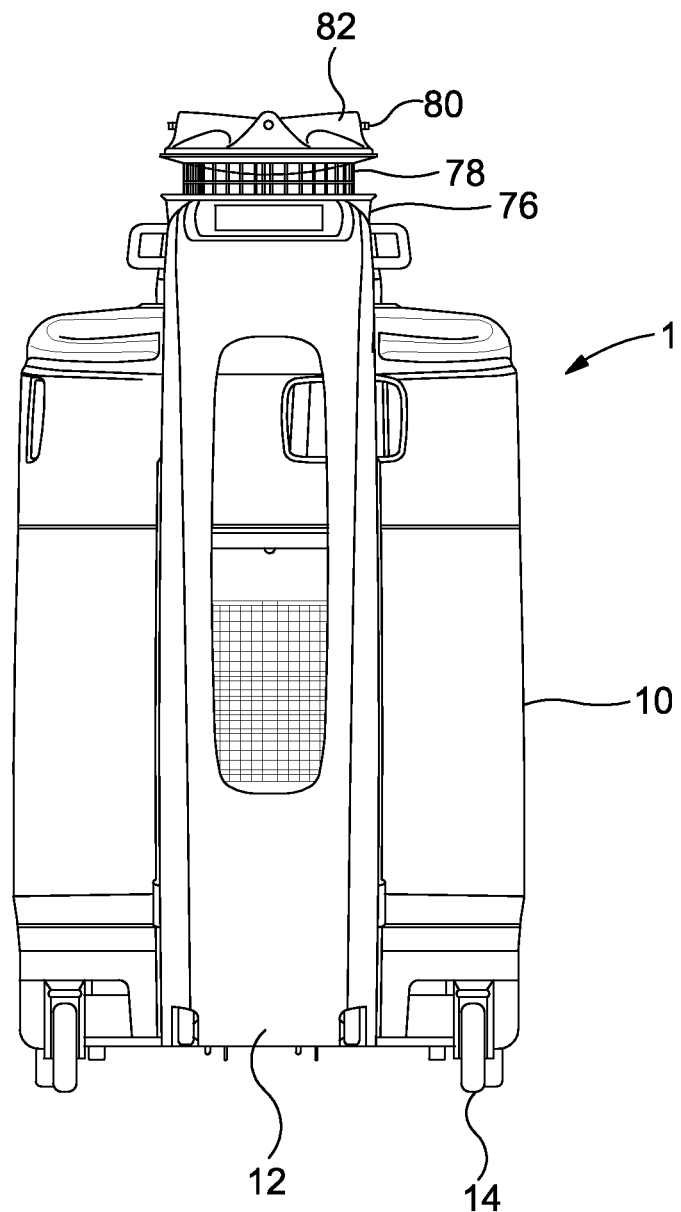
FIG. 3 is a rear elevation external view of the device shown in FIG. 1.

Referring now to the accompanying drawings, there is shown an example of a sterilisation and decontamination device 1. The apparatus comprises a portable enclosure 1 having a main body 10 and a detachable control panel 12. In the embodiment shown, the control panel is in the preferred form of a detachable lectern but it is to be appreciated that the control panel may be provided elsewhere on the enclosure or remote thereto.

The main body 10 has wheels 14 and handles 15 and houses the components of the device (see, in particular, FIG. 6) that are required for carrying out the decontamination process, in particular a humidifier unit and an ozone generator unit. The main body may also include a catalyst assembly 40 and/or a hydrocarbon generator unit for supplying a hydrocarbon containing a carbon-carbon double bond and/or for aiding removal of by-products. A discharge outlet assembly 16 extends from the top of the main body to discharge the required substances into the atmosphere and a microprocessor is provided within the unit for controlling discharge from the outlet assembly.

The humidifier unit generally includes a humidifier, a humidistat sensor, a temperature sensor and a water reservoir 90. The humidifier releases water droplets from the discharge outlet assembly 16. The water droplets have a diameter of less than 5 microns, preferably 2-3 microns, to enhance the rate of evaporation into the atmosphere. The ozone generator unit includes an ozone generator 60, an ozone detector sensor, and an oxygen supply 66 for supplying oxygen to the ozone generator. All these components are housed within or on the housing forming the main body 10—see FIG. 6. A suitable framework may be provided for supporting the various components.

It is to be appreciated that the large number of internal components housed within the packaging of the machine may lead to a bulky and heavy device, making the device less user friendly. Furthermore, the arrangement of the components in a limited space makes maintenance and replacement of individual components more difficult. The present invention provides a removable ozone generator cartridge 60 that allows for fewer parts, reduces the overall space taken up by the components and also allows for easier maintenance and replacement of the ozone generator.

Figure 4:
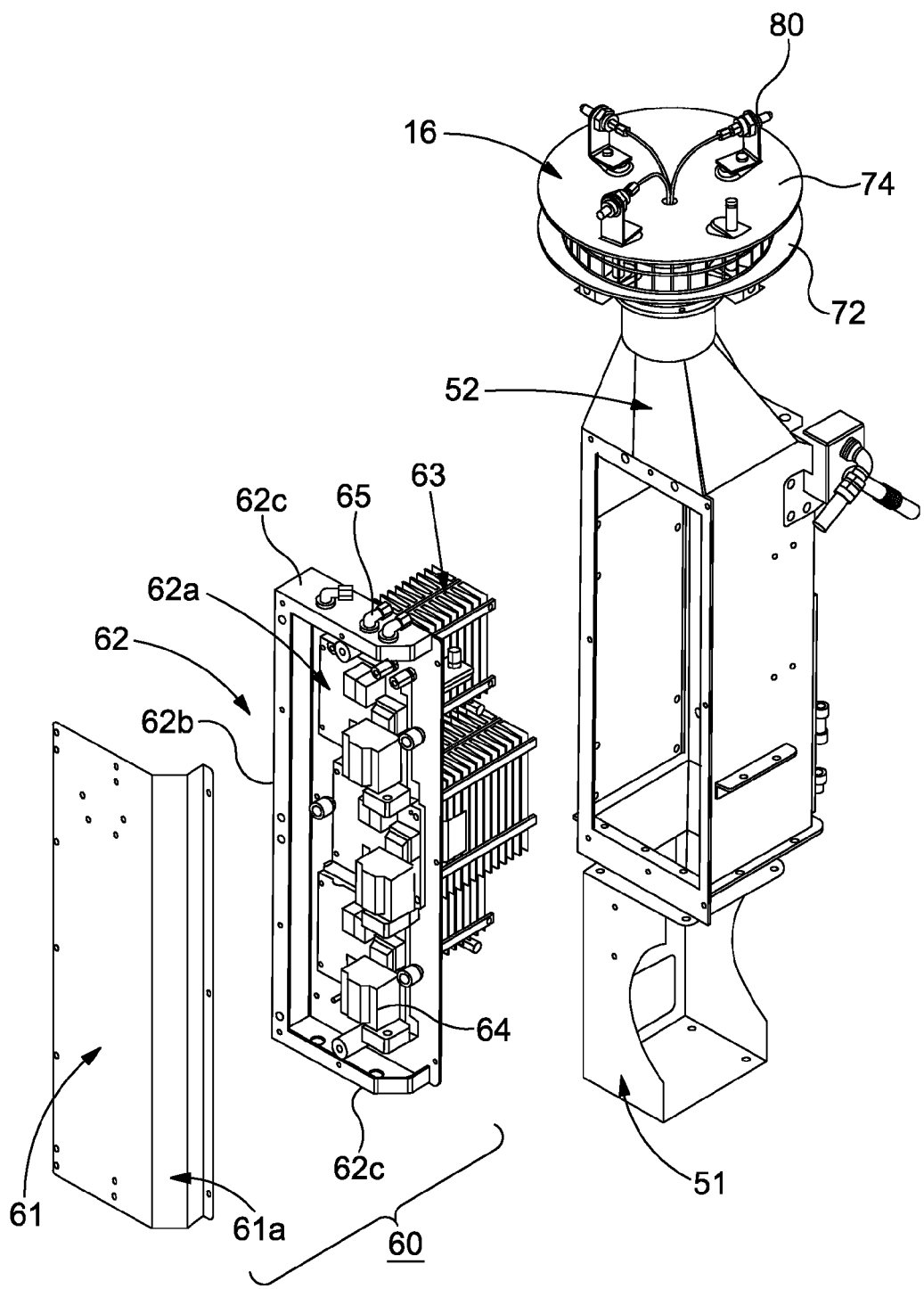
FIG. 4 is an exploded perspective view of certain internal components of the device, specifically showing the ozone generator cartridge according to one embodiment of the present invention, together with the discharge outlet assembly.
Figure 5:
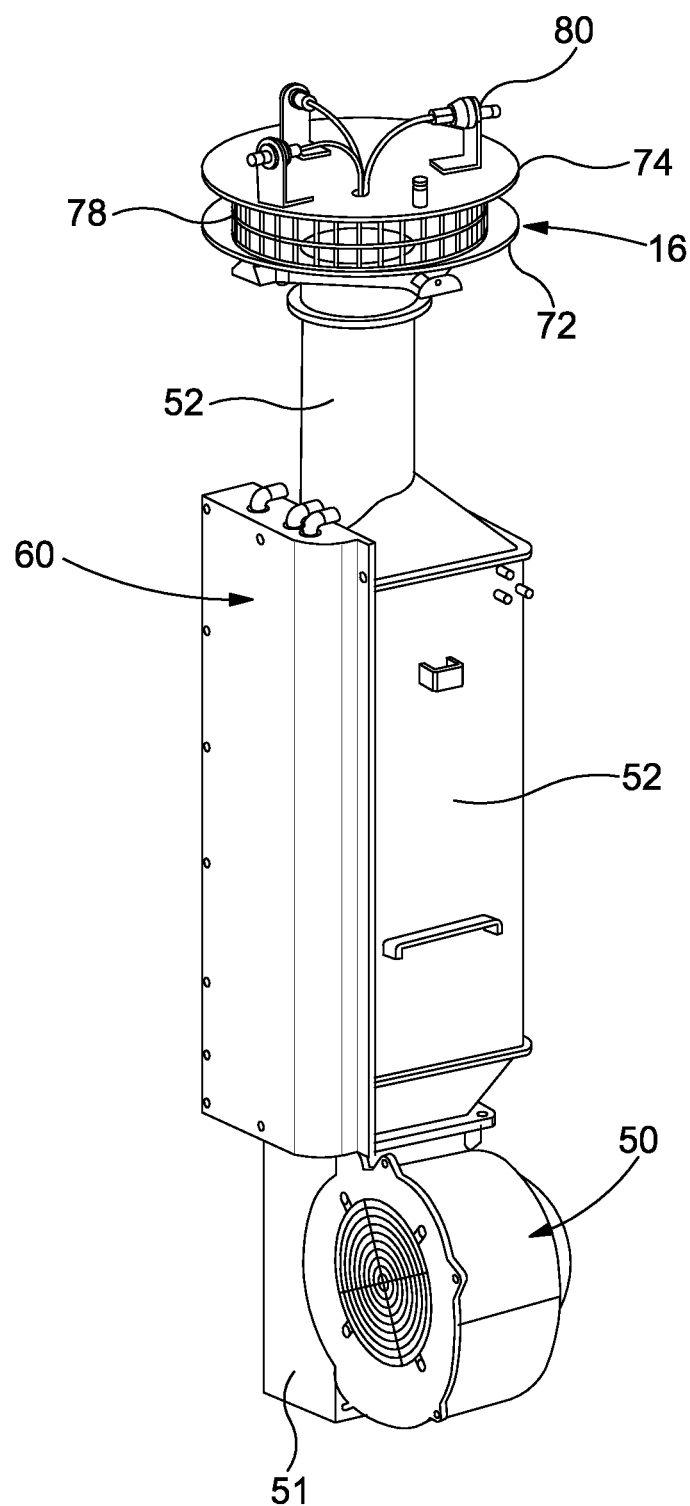
FIG. 5 is a perspective view of the components of FIG. 4, shown assembled together.

In particular, FIGS. 4 and 5 of the accompanying drawings illustrate an ozone generator cartridge according to one embodiment of the present invention. The ozone generator cartridge 60 comprises a housing including a slimline body 62 with a cover 61. The body comprises a flat mounting plate 62a with one long side wall 62b and two short side walls 62c extending substantially orthogonally from the plate. The cover 61 comprises a generally L-shaped panel, the short limb 61a of the cover making up the opposing long side wall in the assembled housing. The intended inner surface of the mounting plate of the body has the components of the ozone generator that must not be exposed to high levels of ozone attached thereto or formed integrally therewith, particularly the high tension power supply units (HT PSUs) 64 and printed circuit boards (PCBs). These components are sealable within the housing by means of the cover 61. Suitable fixing means (not shown) are provided to secure the cover to the body of the cartridge. The housing also has at least one inlet 65 for the introduction of oxygen (or air) for the production of ozone and the connection of a power supply thereto. Extending from the external surface of the mounting plate 62a, away from the interior of the housing, are components of the ozone generator that do not have to be isolated from the path of the ozone, specifically the ozone conversion cell block 63 which in the illustrated example comprises electrodes, dielectric and fins for maintaining the electrical discharge for the production of the ozone, together with an ozone discharge outlet (not shown). The cartridge is also provided with appropriate conduits for delivering the oxygen and ozone through, around and out of the generator.

Figure 6:
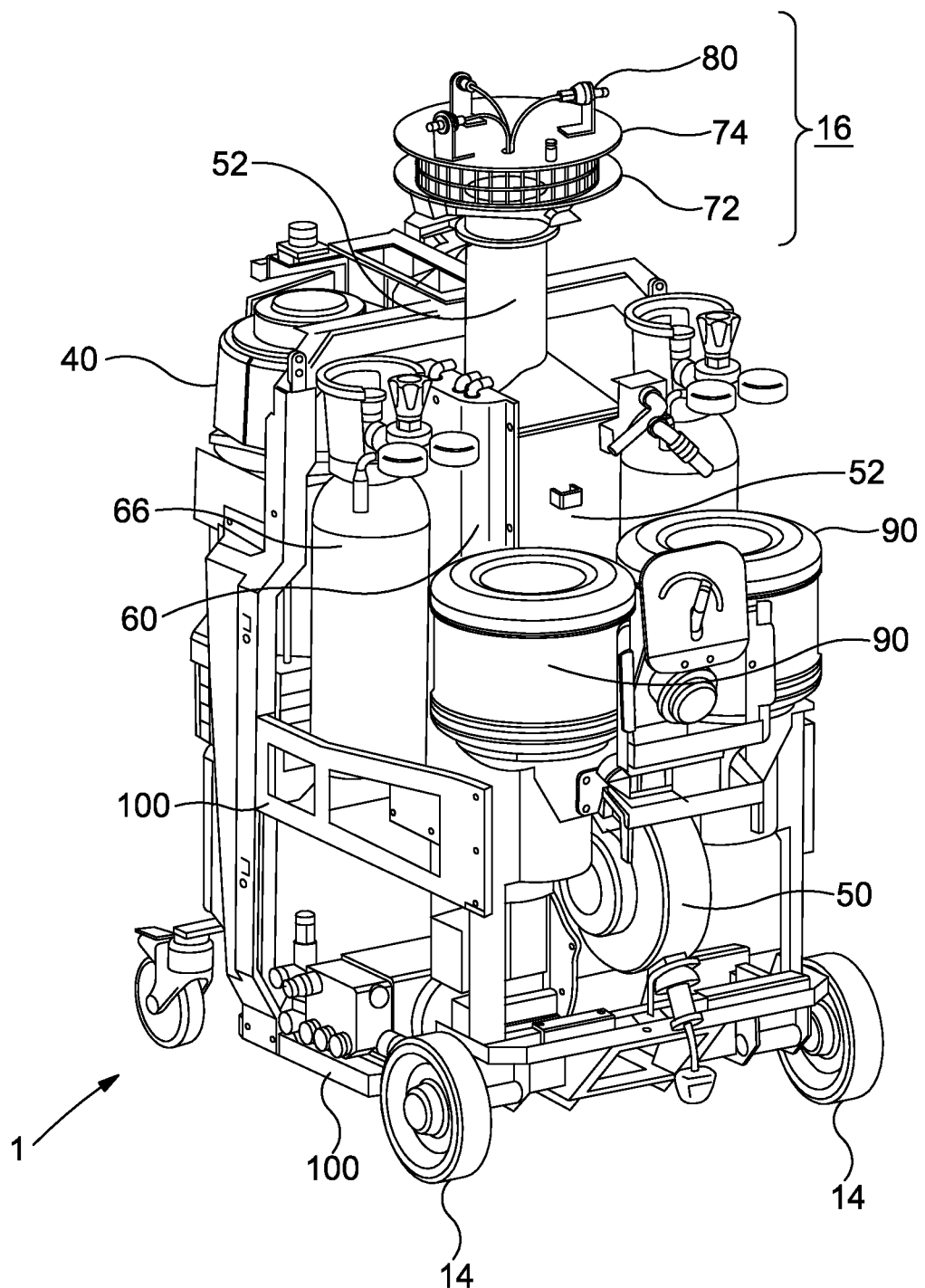
FIG. 6 illustrates the internal components of the sterilisation and decontamination device shown in FIG. 1.

The complete ozone generator cartridge forms the fourth side of a delivery or launch tube 52 within the air decontamination device (see FIGS. 5 and 6). The ozone conversion cell blocks 63 extend transversely across the tube 52 with the other components of the ozone generator being sealed within the housing but positioned against the wall of the launch tube 52. A common fan 50 is provided at the base of a launch tube 52, being supported by a bracket 51 attached to the base of the tube. The upper end of the tube leads to the discharge outlet 16 which comprises a 360 degree high volume air outlet. The discharge outlet assembly comprises a pair of converging plates 72, 74, preferably in the form of discs, between which the air containing the ozone, is discharged. Water discharge nozzles 80 are attached to the upper surface of the top plate 74 to introduce filtered water to a specific formula providing the necessary sterilisation and conductivity to provide effectiveness of humidification application and minimal system maintenance to the atmosphere. One or more water reservoirs 90 deliver water to a compressor (not shown) which in turn delivers high pressure water (at least 50 Bar) to the discharge nozzles. A cover or cap 82 is fitted over the water discharge nozzles, the cover being contoured such as to direct any water to a drainage collection point and a mesh or gauze 78 is provided between the converging plates to prevent the ingress of any foreign objects.

The conduits (not shown) that determine the flow of oxygen and ozone in, through and out of the ozone generator cartridge are preferably arranged to release the bulk of the ozone towards the top of the ozone generator, above the conversion cells 63.

The arrangement of the ozone generator, delivery tube and discharge outlet assembly is such that a single fan can be used not only to create the required airflow but also to provide a cooling airflow for the ozone generators and aid mixing of the ozone within the delivery tube. This is important as 85% to 95% of the electrical energy supplied to a corona discharge ozone generator produces heat which must be removed. Thus, the ability to cool the components of the device whilst simultaneously moving the air through and out of the device has clear financial and weight benefits. The mounting plate of the ozone generator cartridge also acts as a radiator to effect cooling of the internal components of the housing that are mounted on the internal surface of the mounting plate.

If the decontamination device 1 is to include a hydrocarbon discharge unit this too is housed within the main body 10 of the machine and includes a hydrocarbon supply in the form of a tank or container containing the hydrocarbon having a carbon-carbon double bond, such as a secondary olefin, cis or trans, including cyclic olefins together with means to discharge the hydrocarbon through the discharge outlet.

Access to the interior of the main body 10 of the machine is provided by a removable, preferably lockable, side panel or lid. The main body 10 also includes part of a control unit in the form of a microprocessor which controls the apparatus 1 and may be preset with at least one sterilisation and decontamination routine. The control unit includes a controller and a user interface which is located on the detachable lectern 12 by which a user can wirelessly input commands to the main body to remotely control operation of the device.

The apparatus 1 may include an on-board battery and/or may be connectable to a mains power supply. Preferably, the main body 10 may be connected to a mains supply and the lectern 12 is battery-operated, being charged by power from the main body when the lectern is docked therein.

The apparatus 1 will also typically include other safety features, such as safety sensors, and software routines to prevent start-up or initiate shut-down in the event of a system failure.

In use, the whole device 1 comprising the main body 10 connected to the lectern 12 is wheeled into an area which is to be sterilised and/or decontaminated. The unit is correctly positioned and then the lectern is detached from the main body by lifting and tilting the lectern onto its wheels. The lectern is then wheeled out of the room and positioned across a door or other opening that allows access to the area being decontaminated. This acts as a warning and bollard to prevent any person entering the area. Furthermore, the lectern enables operation of the components within the main body to be controlled remotely from outside of the room by means of the user interface connected wirelessly to the microprocessor controlling the main body within the room. During operation of the device, the display unit on the top part of the lectern may display a visible warning to inform personnel that the decontamination process is being carried out and that the area should be left unoccupied. The lectern may also provide a visible or audio message when decontamination is complete, informing the user that the room may be re-occupied. Other appropriate data and information may be stored for access by the user.

During operation of the device, the area is sealed and the control unit located on the main body undertakes appropriate initial safety checks such as checking the relative humidity. If the safety check is not passed, the apparatus 1 does not operate and outputs a suitable indication using warning lights which may be on one or both of the main body and the lectern. During operation of the process, safety checks are made continuously, and in the event of a system failure, the system defaults to a safe mode.

The controller continues to monitor the conditions provided by the device and once a calculated relative humidity level is reached, the controller activates the ozone generator and ozone is generated. Alternatively, the ozone may be generated prior to or simultaneously with the production of the required relative humidity levels. The generated ozone is fed into the discharging humidified airstream that passes through the discharge outlet 16. The controller provides a suitable indication that the ozone generator is operating, and monitors the ambient ozone levels through the ozone detector sensor.

Both the ozone and water vapour concentrations to be detected can be altered by means of the user interface. However a typical setting is 25 ppm v/v of ozone and 13.6 torr. Once the preset ozone and water vapour levels have been detected within the allotted interval, the controller enters a timing phase, known as the "dwell time".

The dwell time can also be altered using the remote user interface, for example, to one hour, and will depend on the degree and type of decontamination/sanitisation to be provided. For instance, contamination by spores or moulds, such as *clostridium difficile*, generally require a longer dwell time than contamination by bacteria, such as listeria and methicillin resistant *staphylococcus aureus* (MRSA).

During the dwell time, the ozone concentration and relative humidity are continuously monitored. If the ozone level falls below a predetermined threshold, the ozone discharge unit is reactivated to replenish the ozone levels. If the humidity falls below the calculated value, the humidifier unit is reactivated to restore the water vapour level.

Again, during the reactivation period, should either the ozone concentration or the relative humidity fail to reach the above-mentioned predetermined minima within a set time interval, for example 10 minutes, the controller aborts the sterilisation and decontamination routine and outputs a suitable indication.

After the dwell time has elapsed, the controller shuts down the various supply units and, if a hydrocarbon is to be supplied, operates a hydrocarbon discharge unit to discharge the hydrocarbon into the ambient environment. The hydrocarbon preferentially reacts with the residual ozone to accelerate the breakdown of the ozone, thereby offering faster user re-entry to the treated area.

When an ozone detector sensor detects that the ozone concentration levels are less than a predetermined value, for example 0.2 ppm or less, the controller shuts off supply of the hydrocarbon and outputs an indication that the sterilisation and decontamination routine is complete. Again this is visible on the user display of the lectern and, optionally, the main body of the machine. The ozone level of 0.2 ppm, depending on the size of the area being sterilised and decontaminated, is usually achieved in less than 3 to 4 minutes.

If the ozone detector sensor fails to indicate that the predetermined safe level of ozone has been reached within a predetermined time interval following introduction of the hydrocarbon, for example within 10 minutes, the controller outputs an indication warning of potentially hazardous ozone levels in the room. The controller may be programmed to allow a time interval to elapse in excess of the standard half-life of ozone before announcing that the room may be re-occupied.

The above-described apparatus utilises a method of producing an artificially high level of non-condensing humidity, and generating in-situ a high concentration of ozone. The materials of the apparatus are resistant to the corrosive effects of ozone and high humidity, and the solvent effects of the hydrocarbon.

It is thus possible to provide a device for decontamination of an area which is fast and effective, discrete and portable. The method may provide better than 99.99% effective sterilisation and/or decontamination of an area without an impact on the environment from harmful by-products. Rapid re-use of a contaminated area can thus be realised. The above-described method has proven to be lethal to a wide variety of pathogens, including bacteria such as Methicillin Resistant *Staphylococcus Aureus* (MRSA). The particular arrangement of the components of the ozone generator enables the ozone cartridge to be repaired and/or replaced easily with the components taking up less space within the machine due to the arrangement of certain components outside the sealed housing. This has the additional benefit of providing these components within the flow path of air circulated by a single fan situated at the base of the delivery tube. Again, this provides clear financial savings, as well as enabling the machine to more compact and lightweight. The internal components of the ozone cartridge, whilst being isolated from high ozone concentrations, are also cooled by the flow of air that contacts the surface of the wall of the cartridge that completes the delivery tube.

The device is able to facilitate both atmospheric and surface decontamination of a hospital room within just one hour. The device is such that is can be wheeled into a vacated room and be activated from outside the room by janitorial staff with minimal training using a simple touch screen control pad. The entire process requires minimal supervision while the intelligent control system constantly monitors room conditions and alerts staff when decontamination is complete or a problem is encountered.

The embodiments described above are given by way of examples only, and other modifications will be apparent to persons skilled in the art without departing from the scope of the invention as defined by the appended claims.

The invention claimed is:

1. An ozone generator cartridge comprising:
    a sealable housing for providing a corona discharge that comprises:
        a plurality of walls defining a cavity, wherein one of the plurality of walls comprises a mounting plate, and wherein the mounting plate comprises an internal surface within the cavity and an external surface outside the cavity that defines an exterior wall of the housing;
    at least one power supply unit within the cavity and directly attached to the inner surface of the mounting plate; and
    at least one inlet within the cavity for connection to an oxygen or air supply; and
at least one ozone conversion cell external to the housing and directly attached to and extending from the external surface of the mounting plate, wherein the ozone generator cartridge comprises the at least one ozone conversion cell directly attached to and extending from the external surface of the mounting plate and the at least one power supply unit directly attached to the inner surface of the mounting plate, and wherein the ozone generator cartridge is configured to sealably engage with an opening of a second housing.

2. An ozone generator cartridge as claimed in claim 1 wherein at least one ozone conversion cell directly attached to and extending from the external surface of the mounting plate comprises at least one pair of electrodes and a dielectric.

3. An ozone generator cartridge as claimed in claim 1 wherein the at least one ozone conversion cell extends substantially orthogonally from the external surface of the mounting plate.

4. An ozone generator cartridge as claimed in claim 1 wherein the housing comprises a body with a cover.

5. An ozone generator cartridge as claimed in claim 4 wherein the body comprises the mounting plate, with one long side wall and two short side walls extending substantially orthogonally from the mounting plate, and the cover comprises a generally L-shaped panel, a short limb of the cover making up an opposing long side wall in the assembled housing.

6. An ozone generator cartridge as claimed in claim 4 wherein the body comprises the mounting plate with one long side wall and two short side walls extending substantially orthogonally from the mounting plate and the cover comprises a generally L-shaped panel, a short limb of the cover making up an opposing long side wall in the assembled housing, and wherein components of the ozone generator cartridge that must not be exposed to high levels of ozone are directly fixed to the internal surface of the mounting plate which is sealable within the housing by means of the cover.

* * * * *